(12) United States Patent
Renn

(10) Patent No.: US 6,444,199 B1
(45) Date of Patent: Sep. 3, 2002

(54) SOLID BORATE-DIOL INTERACTION PRODUCTS FOR USE IN WOUNDS

(75) Inventor: Donald Walter Renn, Glen Cove, ME (US)

(73) Assignee: Advanced Medical Solutions Limited, Winsford (GB)

( * ) Notice: Subject to any disclaimer, the term of this patent is extended or adjusted under 35 U.S.C. 154(b) by 0 days.

(21) Appl. No.: 09/673,912

(22) PCT Filed: Apr. 16, 1999

(86) PCT No.: PCT/GB99/01033

§ 371 (c)(1),
(2), (4) Date: Jan. 9, 2001

(87) PCT Pub. No.: WO99/53968

PCT Pub. Date: Oct. 28, 1999

(30) Foreign Application Priority Data

Apr. 22, 1998 (GB) .............................................. 9808461

(51) Int. Cl.[7] ......................... A61K 31/74; A61K 9/00; A61K 9/70; A61K 9/14

(52) U.S. Cl. .................... 424/78.26; 424/400; 424/443; 424/485

(58) Field of Search .............................. 424/78.26, 400, 424/443, 485; 427/384

(56) References Cited

U.S. PATENT DOCUMENTS 4,624,868 A * 11/1986 Muller ........................ 427/384

* cited by examiner

*Primary Examiner*—Thurman K. Page
*Assistant Examiner*—Blessing Fubara
(74) *Attorney, Agent, or Firm*—Woodard, Emhardt, Naughton, Moriarty & McNett

(57) ABSTRACT

Borate-diol reaction products for wound healing are disclosed. The product is obtained by reacting 0.01–1% by weight of borate with 1–10% by weight of a mixture polyvinyl alcohols. A 1% of the polyvinyl alcohols have viscosities of 25–30 mPa s and 3–10 mPa s.

24 Claims, No Drawings

SOLID BORATE-DIOL INTERACTION PRODUCTS FOR USE IN WOUNDS

The present invention relates to amorphous solid borate-diol interaction products. More particularly, but not exclusively, the present invention relates to solid products formed by interaction of polymeric cis-1,2-diols with borate ion and suited for wound came and other uses.

BACKGROUND OF THE INVENTION

The reaction of sodium tetraborate with cis-1,2-diols to form amorphous solids has been well documented, notably for polyvinyl alcohol, but also for naturally occurring materials such as konjac, guar and locust bean gum. Examples of the use of this reaction to prepare products suited for medical and related purposes are extensive.

EP-A 056,420 describes an eye gel of at least one ophthalmic medicament, polyvinyl alcohol (1 to 3%), a borate gelling agent (0.1 to 1.0%), and sterile water. The gel is maintained at a pH of 6.5 to 8.5, preferably 6.9 to 8.5. The ophthalmic gel is said to be a long acting, topical medicament which has a pH that is compatible with injured eyes and has uniform release characteristics.

U.S. Pat. No. 4,624,868 relates to dried absorbent particles, where guar gum as an exemplification of cis-1,2-diol polysaccharides is first hydrated then thickened by cross-linking with borax and finally dried to a powder to flake form, preferably by freeze drying. The resulting particles can absorb up to 100 times their weight or more of aqueous fluids such as urine and are employed in disposable diapers, bandages, and the like.

U.S. Pat. No. 4,362,781 describes a premoistened wiper comprising a non-woven web impregnated with a modified guar gum (phosphated, 5 to 14% of fiber weight) and wet with an aqueous lotion containing borate ions. The lotion also contains an organic hydroxy or keto acid or salt thereof (such as potassium citrate) capable of completing with borate ions.

U.S. Pat. No. 3,998,215 describes an electrically conductive pad conformable to the surface of the human body and adapted to facilitate the transfer of electrical signals between the body and an electrode. The pad comprises a porous, fibrous carrier having a lightly adherent, conductive hydrogel carried thereby, the hydrogel impregnating and surfacing both sides of the earner and the hydrogel being more cohesive to the hydrogel than adhesive to the surface of the human body to enable residue-free removal from the skin. The hydrogel can comprise a mixture of water, polyvinyl alcohol, sodium borate decahydrate and a fungicide, the water being present in at least about 70% by weight.

PCT/WO 95/17147 relates to fibers coated with particles of a galactomannan, or derivative thereof, cross-linked with borate. Guar and its derivatives are preferred.

U.K. Patent 1,174,139 is concerned with a dilutent composition which comprises a solution comprising;
(A) water,
(B) from 0.5 to 10%, by weight, based on the weight of the solution, of a water-soluble polymer of vinyl alcohol or an ester thereof,
(C) from 0.001 to 5% by weight, based on the weight of the solution, of an alkali metal borate or hydrate thereof, and
(D) from 5 to 10%. by weight, based on the weight of the solution, of a polyol.

Soviet Union Patent 1.795.672 describes a composition which contains (by weight) water 100, polyvinyl alcohol 4.7 to 14.07, sodium tetraborate 0.16 to 0.45, aerosil or white silica 3.75 to 11.25 and an acetamide or acrylamide or saccharose additive 0.23 to 7.5. The product has a gel-like or rubbery consistency and is prepacked in sectioned polyethylene capsules. Prior to use, the prepacked material is chilled in the freezing compartment of a domestic refrigerator. It can produce skin temperatures down to −3 to −7° C. and can be recycled.

DE-A 4,007,668 is concerned with hydrogel foams based on gelatin and water optionally containing polyvinyl alcohol, together with a crosslinking agent which can be boric acid or a borate, and an organic or inorganic acid or salt, optionally with organic plasticizers and/or auxiliary agents and/or additives. The foam can be used for instance in the protection of wounds before drying out.

U.S. Pat. No. 5,071,648 relates to a composition comprising acetalized polyvinyl alcohol complexed with iodine, wherein the composition is capable of releasing free iodine in the presence of water. The acetalized polyvinyl alcohol may be further complexed with a borate. The acetalized PVA is preferably an hydroxylated polyvinyl acetal sponge.

PCT/WO 92/03172 is directed at a bandage, dressing or support matrix having a biocompatible open-pored plastic foam with a hydrogel embedded in the pores. The hydrogel is suitably formed from a borate-modified guar gum.

SUMMARY OF THE INVENTION

The present invention is directed at a different kind of interaction product which can be obtained from reaction of diols with borate. More especially, the present invention is concerned with amorphous solid products formed by interaction of polymeric cis-1,2-diols with borate ion and suited for wound care and other uses. Fluid handling and flow characteristics can be controlled and modified to fill specification needs.

PREFERRED EMBODIMENTS

At pH values between about 7.5 and 8.5, the borate ion from a borate salt or formed in situ from boric acid interacts with polymers containing cis-1,2-diols to form more viscous or amorphous solid systems. The polymeric diols can be synthetic, semi-synthetic, or natural. Some of the more common polymers undergoing this reaction are the polyvinyl alcohols and polysaccharides including galactomannans, such as guar and locust bean-gum, and glucomannans, such as konjac and Aloe (ace) mannans. Depending on the concentration of the polymer or polymers, the borate, and other additives, if any, the consistency can vary from somewhat viscous fluids to crisp amorphous solids. At selected concentrations of the components, the reaction products behave like self-restoring or healable solids that will flow at body temperatures. This property gives them possible value as wound-cavity fillers or wound putties. Other soluble and insoluble components can be added to impart desired properties, such as increased body-fluid absorption or fluid donation.

Although the principle use envisaged for the product of this invention is for the wound cavity-fillers, a number of other medical and non-medical markets can be envisioned. These possible uses include drug delivery, prosthetics and pads (fillers or in situ-formed coatings), and the toy and possibly executive stress-reliever markets.

For use as a wound cavity-filler, the product must be firm enough to handle, yet flow at body temperature to meet wound shape in about 10 to 30 seconds. The product needs to be easy to handle and either absorb or donate moisture, or both. Materials used must be biocompatible, non-toxic, and non-cytotoxic. In this respect, samples of PVA (5% and 20%) with added borate exhibited no cytotoxicity when tested on L929 mouse fibroblasts. Being sterilizable by gamma irradiation, autoclaving, or some other means is desirable.

Preparation of these amorphous solids preferably comprises forming a sol of the diol, and thermostable additives, if any, by dispersing the components in cool water, heating the mixture to boiling, adding hot aqueous sodium tetraborate, and allowing to cool. Other components can be added at suitable temperatures. If film preparation is desired, the hot sol can be distributed on a surface to form a film and the film is then used directly or is dried. For powders or granules, the solid diol can be triturated with a concentrated solution of sodium tetraborate or other borate source, with or without glycerol. For in situ-formed coatings, a sponge, cloth, gauze, or other material to be coated can be dipped into the hot mix, removed and drained, and optionally dried. Alternatively, the coatings can be applied by successively dipping the material to be coated into the borate solution, draining, blotting, blowing, or squeezing to remove the excess, if desired; dipping next into a cis-1,2-diol polymer solution, with or without additives; and finally again into the borate solution. If desired, this series can be repeated.

Spraying or some other means can be used as well as dipping, if appropriate. Again, the finished coated substrate can be maintained moist or partially or fully dried. In any form, the borate interaction products can be prepared and used alone, with internal and/or external supports, or as fillers in permeable or impermeable membranes.

Possible additives to the polymeric cis-1,2-diol reaction mixture used for any of the products are other borate-reactive and/or non-reactive hydrocolloids; reactive or non-reactive low molecular weight substances; insoluble particulates, both swellable and non-swellable, including charcoal and encapsulated chemical and/or biological reagents, ion-exchange resins, etc.; therapeutics; enzymes, antibodies; antimicrobials; etc.

When gelling hydrocolloids, such as agar, agarose, gellan, carrageenan, alginates or curdlan are added to the PVA or other diol before cross-linking, at concentrations where the hydrocolloid alone forms a firm gel, the combinations unexpectedly produce very elastic, almost putty-like compositions which can be stretched into films. The stretched film may have utility as a burn cover as well as a cavity filler. In this respect, the product from 5% PVA with 1.5 to 3.0% agar was particularly interesting.

With the addition of non-gelling hydrocolloids, such as hydroxyethylcellulose (HEC), carboxymethyl cellulose (CMC), and water soluble alginates to the PVA, absorptivity can be increased. The addition of certain borate-reactive polysaccharides, such as guar, can also increase absorptivity.

Polyvinyl alcohols of specific molecular weight ranges and degrees of hydrolysis, alone or as blends of different types, appear to be the best base polymeric cis-1,2-diols. The total concentration of the polyvinyl alcohol can range from 1% to 10% e.g. 5 to 10% (w/w) more or less. The borate is preferably sodium tetraborate used in an amount of 0.4% based on the total weight or 8% based on the weight of the polyvinyl alcohol, though other borate sources can be employed on the same molar basis. PVA types which have found to be most useful are the Polyviol G06/20, its near equivalent Polyviol G04/20 and Polyviol from Wacker Chemicals Ltd., Bridge Street, KT121AS, Walton-on-Thames, Surrey, U.K. The Sigma types P-1763 and P-8136 are similar to the Wacker PVAs. The borate is suitably added as a 2% aqueous solution of anhydrous sodium tetrabotate or as a 3.79% aqueous solution of sodium tetraborate decahydrate (borax), equivalent to the 2% of the anhydrous form.

Compositions of the invention for which the cis-1,2diol is polyvinyl alcohol may be produced so as to be such that when placed in a wound cavity they will flow sufficiently to fill all reaches of the cavity yet remain firm enough to be retained. Such a property is also referred to herein as a "proper flow property" at body temperature. Furthermore, such compositions may have optimum elasticity in that they may be formed into a coherent film, e.g. for use as a bum covering, face mask or similar application.

Details of preferred products in accordance with the invention which may be produced using polyvinyl alcohol as the cis-1,2-diol are given below.

One such preferred product is obtained using 0.1% to 1% by weight of borate and 1% to 10% by weight of a polyvinyl alcohol having a viscosity for 1% solution of 3 to 10 mPa s and a degree of hydroplysis of at least 75. Such a product more preferably comprises 3% to 7%, more preferably 4% to 6% and most preferably about 5% by weight of the polyvinyl alcohol. It is particularly preferred that the viscosity of the polyvinyl alcohol is 4 to 7 mPa s and most preferably about 6 mPa s. Preferably also the polyvinyl alcohol has a degree of hydrolysis of 75% to 85% most preferably about 80%. A particularly suitable example of polyvinyl alcohol for use in this embodiment of the invention is Polyviol G06/20 or its near equivalent G04/20.

Most preferably, the product as defined in the previous paragraph comprises 0.3% to 0.5%, and most preferably about 0.4%, by weight of borate.

A further preferred product is obtained from 0.1% to 1% by weight of borate and 1% to 10% by weight of a polyvinyl alcohol having a viscosity for a 1% solution of 25 to 30 mPa s and a degree of hydrolysis of at least 85%. Such a composition preferably comprises 3% to 7%, more preferably 4% to 6% and most preferably about 5% by weight of the polyvinyl alcohol. It is preferred that the viscosity of the polyvinyl alcohol (for a 1% solution) is 27 to 29 mPa s and most preferably about 28 mPa s. Moreover, it is preferred that the polyvinyl alcohol has a degree of hydrolysis of 85% to 95% and most preferably about 90%. A particularly suitable polyvinyl alcohol meeting these requirements is Polyviol G28/10.

The product as defined in the preceding paragraph preferably comprises 0.3% to 0.5% and most preferably about 0.4% by weight of borate.

A further preferred product in accordance with the invention may be obtained from 0.1% to 1% by weight of borate and a total of 1% to 10% by weight of a first polyvinyl alcohol of relatively low molecular weight and a second polyvinyl alcohol of relatively high molecular weight.

Preferably the ratio of the weight of the first polyvinyl alcohol to the second polyvinyl alcohol is greater than 1:1 and is more preferably 2:1 to 4:1, most preferably about 3:1.

This formulation may comprise a total of 4% to 6% by weight of the first and second polyvinyl alcohols, most preferably about 5% by weight.

The first polyvinyl alcohol is preferably one having a viscosity for a 1% solution of 3 to 10 mPa s, more preferably 4 to 7 mPa s. Preferably also the first polyvinyl alcohol has a degree of hydrolysis of at least 75%, more preferably 75% to 85% and most preferably about 80%. A particularly suitable first polyvinyl alcohol is Polyviol G06/20 or its near equivalent Polyviol G04/20.

The second polyvinyl alcohol is preferably one having a viscosity for a 1% solution of 25 to 30 mPa s, more preferably 27 to 29 mPa s and most preferably about 28 mPa s. Preferably also the second polyvinyl alcohol has a degree of hydrolysis of at least 85%, more preferably 85% to 95% and most preferably about 90%. A particularly suitable polyvinyl alcohol for use as the "second polyvinyl alcohol" is Polyviol G28/10.

The product comprising the mixture of the first and second polyvinyl alcohols preferably comprises 0.3% to 0.5% by weight and more preferably about 0.4% by weight of borate.

A further preferred product is obtained from 0.1% to 1% by weight of borate and 1% to 10% by weight of a polyvinyl alcohol having a viscosity for a 1% solution of 8 to 16 mPa s and a degree of hydrolysis of at least 75%. Such a composition preferably comprises 3% to 7%, more preferably 4% to 6% and most preferably about 5% by weight of the polyvinyl alcohol. It is preferred that the viscosity of the polyvinyl alcohol (for a 1% solution) is 9 to 15 mPa s, more preferably 10 to 14 mPa s. Moreover, it is preferred that the polyvinyl alcohol has a degree of hydrolysis of 75% to 90% more preferably 80 to 85% and most preferably about 82 to 83%.

The product as defined in the preceding paragraph preferably comprises 0.3% to 0.5% and most preferably about 0.4% by weight of borate.

The products as defined in the last but one paragraph have properties similar to those obtained using a mixture of a first polyvinyl alcohol of relative low molecular weight and a second polyvinyl alcohol of relatively high molecular weight.

The above described products comprised of borate and polyvinyl alcohol may additionally comprise a hydrocolloid which may be a reactive hydrocolloid or a non-reactive hydrocolloid. The amount of hydrocolloid may be 1% to 5%, more preferably 2% to 4% by weight of the formulation.

The hydrocolloid may be a gelling hydrocolloid present in the formulation at a concentration at which the hydrocolloid alone forms a firm gel. The gelling hydrocolloid is preferably agar, agaros, gellan, carrageenan, curdalan or a gelling alginate in dissolved or particulate form. The hydrocolloid may be a non-gelling hydrocolloid, preferably hydroxyethyl cellulose or carboxymethyl cellulose.

The elastic wound putties of this invention can be dried into films, supported or unsupported, fully or partially dried, absorb synthetic body fluid and reassume the hydrated elastic composition. This same response occurs with powders of polyols to which borate solution, with or without glycerol, is added and triturated and the powder dried.

The use in controlled-release delivery systems is also envisaged, particularly for compositions having fluid donating properties.

EXAMPLES OF THE INVENTION

The general process for making the borate interaction products comprised the following steps;
1. Dissolving the polymeric cis-1,2-diol by dispersion then heating while stirring.
2. Optionally adding any thermostable components, before or after heating.
3. Dissolving the sodium tetraborate and heating.
4. Combining the sols and mixing.
5. Filling appropriate dispensing containers with hot sol.
6. Autoclaving to sterilize, if desired The test procedure employed in some examples for assessing water absorptivity comprises incubating a known weight of the material to be tested for 30 minutes at 37° C. with a predetermined quantity (40 times sample weight) of Solution A, an aqueous solution at 37° C. containing 142 millimoles of sodium ion and 2.5 millimoles of calcium ions in distilled water, prepared by dissolving 8.298 g of sodium chloride and 0.368 g of calcium chloride dihydrate in distilled water and making up to one liter. The net gain or loss of sample weight is determined and the value converted to uptake or loss per gram of sample.

Example 1
Borate Interaction Products from Konjac, Locust Bean Gum, Guar, and Acemannan Konjac Two grams of konjac powder (Shimizu Propol A, Lot AEH17) was dispersed in 100 ml of distilled water, contained in a 250 ml beaker, using a high shear mixer. The beaker was covered with plastic film and the mixture heated to boiling in a microwave oven. To this 2% sol was added 7 ml of 2% sodium tetraborate (anhydrous) solution. The mixture was stirred well and then allowed to cool. An amorphous, elastic solid resulted. To give this a more self-healing consistency, 2.0 g glycerol may be added to the formulation.

Locust Bean Gum (LBG)

Using the procedure above to prepare the konjac product, 100 ml aqueous sols were prepared of 0.5%, 1.0%, and 1.5% locust bean gum (T-I-C Gums, Lot P00124). To 25 ml portions of each was added 0.5 ml of a solution prepared by adjusting an aqueous 1% boric acid solution to pH 8.6 with 1N NaOH. The mixtures were stirred and allowed to stand. The borate interaction product using 0.5% LBG resembled nasal mucous. The 1.0% was somewhat thicker and sticky, while the 1.5% product was firm, elastic, and self-healing.

Guar

Six grams of guar gum (Lucas Meyer, Emulcol G2) was used to prepare 300 ml of 2% sol using the konjac method above. A portion of the 2% guar sol was diluted to prepare 100 ml each of 1% and 0.5% sols. 200 ml of a 1% solution of anhydrous sodium tetraborate (Fluka) was prepared. To 25 m portions of the guar sols were added various amounts of the borate solution, these mixed thoroughly and the consistencies checked. The products had the following characteristics:

|        | ml of borate |              |                |                 |         |
|--------|--------------|--------------|----------------|-----------------|---------|
| % Guar | 0.5          | 1.0          | 2.0            | 4.0             | 8.0     |
| 2      | fluid        | fluid        | brittle        | brittle elastic | brittle |
| 1      | fluid        | elastic. heals | film elastic | fragile elastic | brittle |
| 0.5    | mucoid       | soft elastic | fragile elastic | not done       | not done |

The brittleness of the 2%/2 ml sample could be reduced by adding glycerol.

Acemannan

Four grams of Aloe vera-derived acemannan (Carrington Labs, 950008) was used to prepare 200 nm of a 2% aceomman sol as described for konjac. While hot, 4 g of glycerol was added and mixed in. To this was added 30 ml of a warm aqueous 5% anhydrous sodium tetraborate (Fluka) solution and the mixture stirred thoroughly. When cool, the borate interaction product was very flexible, self-healing, and stretchable in all directions. When prepared without the glycerol, the product lacked the self-healing property.

Example 2
Borate Interaction Products with Polyvinyl Alcohol (PVA)

PVA preparations from a number of Sources were used to prepare borate interaction products. To prepare 100 ml of aqueous 10% PVA sols, 10 g of PVA was dispersed in 100 ml of distilled water using a high speed mixer. The dispersion was heated in a microwave oven. with occasional stirring, to dissolve the PVA. The lower molecular weight PVAs were dissolved at this point. Some of the higher molecular weight PVAs needed additional treatment using the high shear mixer and additional microwave heating to dissolve them completely. The 100 ml of PVA sol was diluted with 30 ml of distilled water and heated to boiling using microwaves. Twenty milliliters of aqueous 3.79% sodium tetraborate decahydrate (Borax, 20 Mule Team), was heated to boiling using microwaves. This was then added to the hot, diluted PVA sol and the solutions mixed well, giving a 5% PVA/borate interaction product). An increase in viscosity was observed. When cooled, clear, colourless, amorphous solid, self-healing PVA/borate interaction products were obtained. Those prepared using the lower molecular weight PVA were more fluid and conforming than those using the higher molecular weight PVAs, which tended to be more brittle The best of the lower molecular weight, high degree of hydrolysis PVAs were obtained from Sigma-Aldrich Company Ltd. (Fancy Road, Poole, Dorset, BR12 4 QH, England) as P-8136 (Lot 26H1373), from Wacker-Chemicals Ltd. (The Clock Tower, Mt. Felix, Walton-on-Thames, Surrey KT12 IA5, England) as Polyviol G 06/20 (Lot 1), and from BDH Laboratory Supplies, Poole BH15 Ltd., England (as Product 305735B, Lot K22838845 625). The higher molecular weight PVAs yielding satisfactory, more crisp borate interaction products are P1763 (Lot 105H1012) from Sigma-Aldrich and Polyviol G 28/10 (Lot 1) from Wacker-Chemicals.

Example 3
Borate Interaction Products with Combinations of Types of PVA

Mixtures of lower molecular weight PVA and higher molecular weight PVA gave borate interaction products better suited for use as wound putty. Although various ratios were tried, the most satisfactory was a 3:1 mixture.

Components for 500 ml of 5% borate interaction product having 3:1 ratio of lower to higher molecular weight PVA:
- 62 ml of 10% PVA (Polyviol G 28/10) sol prepared as described previously
- 188 ml of 10% PVA (Polyviol G 06/20) sol prepared as described previously
- 150 ml of distilled water
- 100 ml of aqueous 3.79% sodium tetraborate decahydrate solution.

The PVA sols and the distilled water were mixed thoroughly and brought to boiling using a microwave oven (beaker covered with a plastic film). The borate solution was brought to boiling temperature using microwaves and added to the hot PVA sol. This sol was stirred thoroughly using a spatula, then allowed to cool. The resulting product was a clear, colourless, self-healing, flowable amorphous solid.

Alternatively, 30 ml of the hot sol, with all the components, was placed in each of 15, 30-ml wide-mouthed clear polycarbonate jars. These were subsequently autoclaved to give sterile samples.

Example 4
Body Fluid-absorptive Borate/PVA Composites with CMC, HEC

In the test procedure for water absorptivity, the PVA/borate interaction products donated water rather than absorbed it. To make the products water absorptive, water soluble hydrocolloids can be added.

With Added CMC

The following sols were prepared: (a) 200 ml of 10% PVA (BDH, Product 305735B, Lot K22838845 625) and (b) 100 ml of 6% carboxymethylcellulose (CMC) (Aqualon, Blanose Type 7H4XF, Lot 22-8623). The borate solution used was 2% aqueous anhydrous sodium tetraborate (Fluka). PVA/borate interaction products having the following compositions were prepared as described previously, with the CMC sols being added before heating the PVA.

|          | 10% PVA | 6% CMC   | Water    | 2% Borate |
|----------|---------|----------|----------|-----------|
| 2% CMC   | 75 ml   | 50 ml    | 0 ml     | 25 ml     |
| 0.5% CMC | 75 ml   | 12.25 ml | 37.75 ml | 25 ml     |

With added HEC: Same as the 2% CMC preparation except hydroxyethylcellulose (Aqualon, Natrosol, 250HHX pharm., Lot M-1145) was substituted for the CMC.

The test procedure for water absorptivity gave the following results:

| | |
|---|---|
| 5% PVA/borate | −0.200 g Solution A/g product |
| With 0.5% CMC | −0.197 g Solution A/g product |
| With 2.0% CMC | +0.331 g Solution A/g product |
| With 2.0% HEC | +0.390 g Solution A/g product |

Example 5
Gelling Hydrocolloid-modified Borate/PVA Composites

In order to strengthen the PVA/borate interaction product and make it less flowing and more gel-like for possible use as breast prostheses, gelling hydrocolloids were included in the PVA sol.

To 10 g of white purified agar (Sigma, Lot 56H04261) was added 150 ml of distilled water and the mixture stirred until all the agar was wet. This was followed by the addition of 250 ml of a 10% aqueous sol of PVA (Wacker Polyviol, G06/20, Lot 1), the mixture stirred well and heated to boiling using a microwave oven. To this was added 100 ml of hot aqueous 3.79% sodium tetraborate solution. The solutions were mixed thoroughly and permitted to cool. A white, translucent, somewhat waxy amorphous solid resulted that could be stretched to a thin film and was self-healing. The absorption for the 2% agar product was +0.10 g Solution A/g product Thus, surprisingly, the agar did not form a gel structure and the product remained amorphous, but with unique strong elastic, yet self-healing qualities. While the gelling hydrocolloid added in this example was white purified agar (Sigma, Lot 56H04261), other gelling hydrocolloids gave similar products. These are agar (Oxoid Agar No. 3 Technical, Lot 183 61849), iota-carrageenan (Luxura 5211, Arthur Branwall & Co., Ltd.), gellan (Monsanto, Kelcogel Lot 41420), gellan plus magnesium ion, and curdlan (Takeda, Lot IS08B), agarose and gelling alginates.

Similar products could be obtained using Wacker Polyviol G04/20.

Example 6
Reconstitutable Films of the Borate Interaction Product PVA/borate/glycerol Glycerol (1% w/w) was added to hot liquid PVA/borate sol and the mixture was poured as a thin layer into a polished-surface stainless steel pan. This was placed into a 65° C. forced-air oven to dry. The resulting film was clear, colourless, and flexible and imbibed liquid to become elastic and self-healing when placed in Solution A. Partial drying resulted in a thicker, clear elastic pad.
Guar/borate/glycerol Glycerol (1% w/w) was added to hot liquid 1% guar/borate sol and the mixture was poured as a thin layer into a polished-surface stainless steel pan. This was placed into a 65° C. forced-air oven to dry. The resulting film was clear, colourless, and flexible and imbibed liquid to become elastic and self-healing when placed in Solution A.

Example 7
Reconstitutable Borate Interaction Product Granules

The polymeric cis-1,2-diol can be mixed with a small amount of glycerol, some borate added and mixed in well. This can be dried fully or partially dried and when contacted with saline, will form a putty-like mass.
Guar/borate To 10 g of guar (Meypro, CSA 200/50, Control No. 14827) was added 3 ml of 2% aqueous anhydrous sodium tetraborate and the mixture granulated thoroughly using a spatula. This was followed by the addition of 2 g of glycerol, mixed in thoroughly with a spatula. This mixture appeared to be dry granules. When a sample was covered with Solution A, in 5 minutes all fluid had been absorbed and the granules became joined in a putty-like state.
PVA/borate The same procedure was followed for PVA (BDH, Lot 5876230B). The granulated product was less absorptive and took significantly longer to reconstitute.

Example 8
In situ-formed Coatings of Borate Interaction Product

A piece of polyurethane foam cut into the shape of a breast prosthesis was dipped into a 3.79% sodium tetraborate decahydrate (borax) solution then the excess removed by squeezing. The foam was next dipped into a 10% sol of PVA (Wacker Polyviol G28/10, Lot 1), then held vertical to drain the excess. Finally, the foam was dipped into the borate solution and again the excess removed by holding in a vertical position. The tough PVA/borate interaction product was fully adhered to the foam. The coated foam was maintained in a moist condition.

Example 9
Therapeutic Delivery System

The borate interaction products can be used as controlled-release delivery systems. As a demonstration example, a small portion of a glycerol/iodine tincture/sugar paste, prepared for another project, was blended into a 5% PVA/borate interaction product.

Example 10
Borate Interaction Products with Combinations of PVA and Alginate
Ex. 10.1

To 5 g of high mannuronic acid-containing sodium alginate (ProNova Protanal HF120RB3) in a 250-ml beaker was added rapidly 30 ml of distilled water and the mixture worked into a homogeneous paste using a spatula. To this was added 50 g of a 10% sol of polyvinyl alcohol (Polyviol G06/20, Wacker Chemicals Ltd.), the mixture blended thoroughly, the beaker covered with plastic film, and the contents heated to boiling several times using microwaves. To the hot sol was added 20 ml of hot 3.79% sodium tetraborate decahydrate (Borax, Twenty Mule Team), the mixture stirred well and reheated to boiling. Upon cooling, a stiff amorphous solid was produced that could be stretched into a tough film.
Ex. 10.2

The procedure of Ex 10.1. was repeated except that half (10 ml) of the borax solution was added. The resulting product was softer, more elastic and somewhat sticky.
Ex. 10.3

The procedure of Ex 10.1 was repeated except that 2.5 g of the alginate was used. The product was easily fractured and had a moist surface.
Ex. 10.4

The procedure of Ex 10.1 was repeated except that 1.0 g of the alginate was used. The product, like that containing 2.5% alginate (Ex 10.3) had a moist surface and was easily fractured.

Example 11
Borate Interaction Products with Combinations of PVA and LMP

The procedure of Example 10.1 was repeated except that 2.0 g of low methoxyl pectin (Citrus Colloids E440. Type 194, Batch 3052) was used. Because of the low pH associated with this material and the need to have a pH of about 7.5 to 8.5 for the borate interaction with the PVA, the pectin/PVA sol was neutralized with sodium hydroxide before the borate was added. The borate interaction product was initially quite flexible and self-healing. Upon standing, the surface became moist, even in a closed system and eventually separated into liquid and solid phases. If the sol was not reheated after adding the borate, this separation could be retarded.

Example 12
Borate Interaction Products with Combinations of PVA and CMC.

The procedure of Example 10.1 was repeated except that 5.0 g of CMC (Aqualon Blanose, lot 62762) was used. The product was translucent, fracturable, semi-self healing, and somewhat moist.

Example 13
Borate Interaction Products with Combinations of PVA and HEC.

The procedure of Example 10.1 was repeated except that 5.0 g of HEC (Aqualon Natrosol Type 250M pharm, lot M-0117) was used. The product was transparent, elastic, tough, and self-healing.

Example 14
Borate Interaction Products with Combinations of PVC and SSP.

The procedure of Example 10.1 was repeated except that 2.0 g of Citrus Colloids Type 128, batch 3780/3 slow-set pectin was used (SSP) was used. A tough resilient product was initially formed, the product separating when reheated.

Example 15
Borate Interaction Products with PVA and Alginate Fibres.

To 5.0 g of NaCa alginate fibres (Ex Innovative Technologies) was added 25 ml of distilled water and the mixture stirred with a spatula until a uniform dispersion was obtained. To this, was added 150 ml of the hot, melted product of Example 3. The mixture was stirred to uniformity with a spatula. A white, translucent, elastic mass resulted.

Example 16

Solution A absorption studies on the products of Examples 10 to 15 gave the following results.

| Example No. | Sample Description (PVA/borate with) | Absorption of Solution A (g/g) |
|---|---|---|
| 1 | 10.1 Alginate | 1.72 |
| 2 | 10.2 Alginate | 2.45 |
| 3 | 10.3 Alginate | 0.58 |
| 4 | 10.4 Alginate | 0.65 |
| 5 | 11 Low-methoxylpectin | 0.03 |
| 6 | 12 CMC | 0.92 |
| 7 | 13 HEC | 1.20 |
| 8 | 14 Slow-Set Pectin | 0.07 |

When the preparations were kept in Solution A for 42 hours, all except 1,2 and 7 disintegrated. These, though swollen, maintained their integrity.

Example 17

Selected samples were subjected to further fluid absorption/donation studies.

Fluid absorption studies were carried out to determine fluid absorption from a 2% agar gel prepared by dissolving 20 g agar powder in 980 g of Solution A. To carry out the absorption test, a piece of net (aperture Size 100 μm) was placed onto a known weight of the agar gel. A known weight of the sample under test was then applied to cover the net. The "assembly" was incubated for 48 hours at a temperature of 26 to 28° C., after which the net and sample were removed and the agar reweighed. Specific absorption was defined as the weight decrease in the agar divided by the original weight of the sample.

The fluid donating test was carried out to determine fluid donation to 30% gelatin (made up with Solution A) using a procedure analogous to the absorption test but determining the weight increase of the gelatin. Specific donation to the gelatin was defined as the weight increase of the gelatin divided by the weight of the sample.

The samples tested and the results obtained are shown in the following table.

| Example | Sample Description | Specific Donation | Specific Absorption |
|---|---|---|---|
| 2 | PVA Mixture | 0.588 | −0.055 |
| 5 | PVA Mixture Containing 2% Purified Agar | 0.364 | −0.036 |
| 13 | PVA/HEC | 0.226 | 0.202 |
| 10 | PVA/Alginate | 0.131 | 0.551 |
| 15 | PVA/Alginate Fibres | 0.269 | −0.083 |

Example 18

Films were prepared from selective borate-interaction products. These elastic amorphous solid preparations were spread evenly on the bottom of plastic petri dishes and dried at 20° C. in a forced air oven. Portions were then placed in Solution A and their behavior observed. The following table summarizes the results.

| Sample Description | Film Properties | Hydration characteristics | |
|---|---|---|---|
| | | 0.5 hr | 18 hrs |
| PVA/borate/2% agar | near clear, flexible | slow uptake | disintegrated |
| Mixed PVA (3:1)/borate | clear, flexible | slow uptake | disintegrated |
| PVA/borate/5% alginate | clear, flexible, a bit pocked | rapid uptake | maintained integrity |
| PVA/borate/5% HEC | nearly clear, flexible | rapid swelling | maintained integrity |

What is claimed is:

1. A borate-diol interaction product comprising a 1% to 10% by weight of polyvinyl alcohol and 0.1% to 1% by weight of borate wherein the polyvinyl alcohol comprises a first polyvinyl alcohol having a viscosity for a 1% solution of 3 to 10 mPa s and a second polyvinyl alcohol having a viscosity for a 1% solution of 25 to 30 mPa s.

2. A product as claimed in claim 1 comprising a total of 4 to 6% by weight of polyvinyl alcohol.

3. A product as claimed in claim 2 comprising a total of about 5% by weight of polyvinyl alcohol.

4. A product as claimed in claim 1 wherein said viscosity of the first polyvinyl alcohol is 4 to 7 mPa s.

5. A product as claimed in claim 4 wherein said viscosity of the first polyvinyl alcohol is about 6 mPa s.

6. A product as claimed in claim 1 wherein the first polyvinyl alcohol has a degree of hydrolysis of at least 75%.

7. A product as claimed in claim 6 wherein the first polyvinyl alcohol has a hydrolysis of 75% to 85%.

8. A product as claimed in claim 7 wherein the first polyvinyl alcohol has a degree of hydrolysis of about 80%.

9. A product as claimed in claim 1 wherein said viscosity of the second polyvinyl alcohol is 27 to 29 mPa s.

10. A product as claimed in claim 9 wherein said viscosity of the second polyvinyl alcohol is about 28 mPa s.

11. A product as claimed in claim 1 wherein the second polyvinyl alcohol has a degree of hydrolysis of at least 85%.

12. A product as claimed in claim 11 wherein the second polyvinyl alcohol has a degree of hydrolysis of 85% to 95%.

13. A product as claimed in claim 12 wherein the second polyvinyl alcohol has a degree of hydrolysis of about 90%.

14. A product as claimed in claim 1 comprising 0.3% to 0.5% by weight of borate.

15. A product as claimed in claim 14 comprising about 0.4% by weight of borate.

16. A product as claimed in claim 1 additionally comprising a hydrocolloid.

17. A product as claimed in claim 16 wherein the hydrocolloid is present in an amount of 1% to 5% by weight.

18. A product as claimed in claim 17 wherein the hydrocolloid is present in an amount of 2 to 4% by weight.

19. A product as claimed in claim 16 wherein the hydrocolloid is a gelling hydrocolloid present at a concentration at which the hydrocolloid alone forms a firm gel.

20. A product as claimed in claim 19 wherein the gelling hydrocolloid is agar, agarose, gellan, carrageenan, curdlan or a gelling alginate.

21. A product as claimed in claim 16 wherein the hydrocolloid is a non-gelling hydrocolloid.

22. A product as claimed in claim 21 wherein the non-gelling hydrocolloid is hydroxyethylcellulose or carboxymethyl cellulose.

23. A product as claimed in claim 16 wherein the hydrocolloid, is selected from a non-reactive hydrocolloid, a reactive hydrocolloid, a non-gelling hydrocolloid or a gelling hydrocolloid.

24. A product as claimed in claim 20 wherein the gelling hydrocolloid is in a dissolved form or a particulate form.

* * * * *